US008642095B2

(12) United States Patent
Sommerfeld et al.

(10) Patent No.: US 8,642,095 B2
(45) Date of Patent: Feb. 4, 2014

(54) DIETARY COMPOSITION AND METHOD OF USING THE SAME

(75) Inventors: Audrey Sommerfeld, Hermosa Beach, CA (US); Steve Witherly, Valencia, CA (US)

(73) Assignee: ViSalus Holdings, LLC, Troy, MI (US)

( * ) Notice: Subject to any disclaimer, the term of this patent is extended or adjusted under 35 U.S.C. 154(b) by 653 days.

(21) Appl. No.: 12/571,252

(22) Filed: Sep. 30, 2009

(65) Prior Publication Data

US 2010/0080863 A1    Apr. 1, 2010

Related U.S. Application Data

(60) Provisional application No. 61/101,305, filed on Sep. 30, 2008.

(51) Int. Cl.
*A61K 36/00* (2006.01)
*A61K 36/82* (2006.01)
*A23L 2/00* (2006.01)
*A23L 1/30* (2006.01)

(52) U.S. Cl.
USPC .............. 424/725; 424/729; 426/590; 426/72

(58) Field of Classification Search
None
See application file for complete search history.

(56) References Cited

U.S. PATENT DOCUMENTS

| | | | |
|---|---|---|---|
| 5,229,390 A | 7/1993 | Moriyama et al. | |
| 5,778,894 A * | 7/1998 | Dorogi et al. | 128/898 |
| 6,299,925 B1 | 10/2001 | Xiong et al. | |
| 6,462,051 B1 | 10/2002 | Nozawa et al. | |
| 6,514,544 B2 | 2/2003 | Fuchs et al. | |
| 2004/0198754 A1 * | 10/2004 | McKee et al. | 514/263.34 |
| 2005/0048136 A1 * | 3/2005 | Choudhry | 424/725 |
| 2007/0141122 A1 * | 6/2007 | Reulein | 424/439 |

FOREIGN PATENT DOCUMENTS

JP    09059161 A  *  3/1997

OTHER PUBLICATIONS

Neuro: Smart Energy, Refresh Your Mind, and Your Body With a Portable Energy Drink Mix That's Good for You! May 17, 2007, www.visalus.com, pp. 1.
Nikolic, Jelenka, et al., Effect of Caffeine on Metabolism of L-arginine in the Brain, Molecular and Cellular Biochemistry, 244, 2003, pp. 125-128.
Fuel Your Genius, Visalus Life, Health, Prosperity, Seeds of Change . . . , Omaha, May 17, 2007, pp. 1-25.
Visalus Neuro FAQ, Neuro Smart Energy, www.visalus.com, Apr. 9, 2007, pp. 1-2.
Kim, Woojae, Debunking the Effects of Taurine in Red Bull Energy Drink, Nutrition Bytes, 9(1), 2003, pp. 1-8.

\* cited by examiner

*Primary Examiner* — Qiuwen Mi
(74) *Attorney, Agent, or Firm* — Vedder Price P.C.

(57) ABSTRACT

According to one aspect of the present invention, a dietary composition is provided. In at least one embodiment, the dietary composition comprises a therapeutically effective amount of an admixture including a caffeine ingredient and a vasodilator ingredient. In at least another embodiment, the admixture further includes an additive selected from the group consisting of taurine, rhodiola, green tea extract, dimethylethanolamine, inositol, vitamin C, one or more B vitamins, a flowing agent, citrulline malate, and combinations thereof. In certain particular embodiments, the caffeine ingredient includes dicaffeine malate. In certain other embodiments, the vasodilator ingredient includes diarginine malate.

19 Claims, No Drawings

DIETARY COMPOSITION AND METHOD OF USING THE SAME

CROSS-REFERENCE TO RELATED APPLICATIONS

This application claims the benefit of U.S. Provisional Application Ser. No: 61/101,305 filed Sep. 30, 2008, with the entire contents thereof incorporated herein by reference.

BACKGROUND

1. Technical Field

One aspect of the present invention relates to a dietary composition. Another aspect of the present invention relates to a method of using a dietary composition.

2. Background Art

Dietary compositions such as the so-called energy drinks are typically designed to give the user a burst of energy after oral consumption of the energy drink. Some energy drink formulations include a combination of methylxanthine, B vitamins, and exotic herbal ingredients.

SUMMARY

In one or more embodiments, dietary composition, stimulant beverage compositions and beverage concentrates adapted for oral administration with water or other liquids, such as juices, iced tea, tea, and soda are disclosed. The compositions may be added to any hot or cold beverage, for example, iced tea, hot water or hot tea. In one embodiment, the composition includes a relatively low concentration of caffeine, a vasodilator ingredient, taurine, rhodiola, an extract of green tea, dimethylethanolamine, inositol, vitamin C and/or B vitamins. In another embodiment, a method for increasing energy and mental alertness of an individual, such as a human or an animal, is provided.

In one embodiment, a composition including caffeine and a vasodilator ingredient is disclosed. In another embodiment, a composition including caffeine, a vasodilator ingredient and taurine is disclosed. In yet another embodiment, a composition including caffeine, a vasodilator ingredient, taurine and rhodiola is disclosed. In one embodiment, a composition including caffeine, a vasodilator ingredient, taurine, rhodiola and extract of green tea is disclosed. In another embodiment, a composition including caffeine, a vasodilator ingredient, taurine, rhodiola, extract of green tea and dimethylethanolamine is disclosed. In yet another embodiment, a composition including caffeine, a vasodilator ingredient, taurine, rhodiola, extract of green tea, dimethylethanolamine, inositol, vitamin C and B vitamins is disclosed. In yet another embodiment, a composition including caffeine, a vasodilator ingredient, taurine, rhodiola, extract of green tea, dimethylethanolamine, inositol, vitamin C and B vitamins, and di-citrulline malate is disclosed. The B vitamins may be niacinamide B3, pantothenic acid B5, pyridoxine (HCl) B6, thiamin (mononitrate) B1, Biotin B7 (H), and/or vitamin B12 (cyanocobalamin 1%). In certain embodiments, the dimethylethanolamine is used in powder form.

In one embodiment, the composition includes the following weights of the following ingredients: from about 5 mg to 150 mg dicaffeine malate; from about 50 mg to 5 grams diarginine malate; from about 10 mg to 2 grams Taurine; from about 10 mg to 1 gram Rhodiola with 3% rosavins; from about 10 mg to 1 gram Green Tea with 50% polyphenols; from about 10 mg to 1 gram dimethylethanolamine ("DMAE") bitartrate; from about 10 mg to 1 gram Vitamin C (sodium ascorbate), 100% reference daily intake ("RDI"); from about 5 to 250 mg Inositol; from about 1 to 50 mg Niacinamide B3, 100% RDI; from about 1 to 50 mg Pantothenic acid B5, 200% RDI; from about 1 to 30 mg Pyridoxine (HCl) B6, 300% rdi; from about 1 to 30 mg Thiamin (mononitrate) B1, 200% RDI; from about 0.1 to 1 mg Biotin B7 (H), 100% RDI; and from about 0.05 to 10 micrograms Vitamin B12 (cyanocobalamin 1%) 200% RDI.

In one embodiment, any of the above-identified compositions may include carbonated water, uncarbonated water, flavoring ingredients, and natural sweeteners, such as sucralose.

In another embodiment, a method of increasing energy and mental alertness is disclosed which includes the step of administering to an individual any of the above-identified compounds. The composition can be provided in a concentrated form to be added to a liquid and served as a ready-to-drink beverage product.

In one or more embodiments, dietary composition, stimulant beverage compositions and beverage concentrates adapted for oral administration with water or other liquids, such as juices, iced tea, tea, and soda are disclosed. In one embodiment, the composition includes a relatively low concentration of caffeine, a vasodilator ingredient, taurine, rhodiola, an extract of green tea, dimethylethanolamine, inositol, vitamin C and/or B vitamins

DETAILED DESCRIPTION OF EMBODIMENTS

Except where expressly indicated, all numerical quantities in this description indicating amounts of material or conditions of reaction and/or use are to be understood as modified by the word "about" in describing the broadest scope of the present invention. Practice within the numerical limits stated is generally preferred.

The description of a single material, compound or constituent or a group or class of materials, compounds or constituents as suitable for a given purpose in connection with the present invention implies that mixtures of any two or more single materials, compounds or constituents and/or groups or classes of materials, compounds or constituents are also suitable. Also, unless expressly stated to the contrary, percent, "parts of," and ratio values are by weight. Description of constituents in chemical terms refers to the constituents at the time of addition to any combination specified in the description, and does not necessarily preclude chemical interactions among constituents of the mixture once mixed. The first definition of an acronym or other abbreviation applies to all subsequent uses herein of the same abbreviation and applies mutatis mutandis to normal grammatical variations of the initially defined abbreviation. Unless expressly stated to the contrary, measurement of a property is determined by the same technique as previously or later referenced for the same property.

According to one aspect of the present invention, there is provided a dietary composition containing a therapeutically effective amount of an admixture including a caffeine ingredient and a vasodilator ingredient. In one or more embodiments, the dietary composition is formulated as water-based beverage commonly referred to as "energy drinks;" and the admixture is the corresponding beverage concentrate adapted for formulating the water-based beverage. The admixture can be in the form of packed dry powder, pellets, pills, granules, or any other suitable shapes. The thus formulated "energy drinks" may contain various natural ingredients that have stimulating effects and increase physical endurance, treat fatigue and/or improve nervous system functions. One or more formulations of the present invention may provide an "energy boost."

In one or more embodiments, the term a "therapeutically effective amount" refers to an amount of the admixture of the dietary composition, when orally administered to a subject, effects a reduced sensation of fatigue and/or an increased sensation of energy as can be felt by the subject, within a reasonable lapse of time after the oral administration.

The exact value of a therapeutically effective amount varies based upon the sensitivity and size of each subject, and is readily determinable by one of skill in the art using conventional procedures for the routine administration of effective dose. By way of example, the therapeutically effective amount varies with the physical characteristics of the subject, such as age, gender, and weight; and is dependent upon any disease state the subject may be associated with. Typically, the therapeutically effective amount is configured as a daily dose of 2.5 to 6.5 grams, 3.0 to 6.0 grams, 3.5 to 5.5 grams, or 4.0 to 5.0 grams in dry weight of the admixture containing various ingredients as described herein.

The reasonable time needed for the reduced sensation of fatigue and/or an increased sensation of energy to be felt by the subject varies with the physical characteristics of the subject, such as age, gender, and weight and is dependent upon any disease states the subject may be associated with. Typically, the reasonable time is a time period of 1 to 12 hours, 2 to 10 hours, 3 to 8 hours, or 4 to 6 hours.

In one or more embodiments, the caffeine ingredient includes a xanthine alkaloid compound that acts as a stimulant in humans, and its derivatives, guaranine found in guarana, mateine found in mate, and/or theine found in tea. Methylxanine is a methylated derivative of xanthine. Several classes of methylxanthines are caffeines, theobromine, as well as, theophylline and its synthetic analog aminophylline (theophylline ethylenedamine), which has shorter duration of action, is less potent, and contains only 78 percent to 86 percent by weight of theophylline. In certain particular embodiments, the caffeine ingredient includes dicaffeine malate, which in one form, delivers 75% caffeine. Typically, the dicaffeine malate can be included in an amount of 0.1 to 15 percent by weight, 0.5 to 10.0 percent by weight, 1.0 to 5.0 percent by weight, or 1.25 to 1.75 percent by weight of the total weight of the admixture.

In one or more embodiments, the vasodilator ingredient refers to molecules that effect vasodilation of blood vessel possibly through regulating one or more of the following intercellular components: calcium channels, cyclic AMP, and cyclic GMP. The vasodilator ingredient can include arginine (2-amino-5-guanidinopentanoic acid) in one or more available zwitterionic forms, diarginine malate, nitric oxide, histamine, prostacyclin, prostaglandin E2, bradykinin, substance P, platelet activating factor, or combinations thereof. Without being limited to any theory, it is believed that arginine, wherein included may assist in the cellular uptake of caffeine. Arginine, as well as other vasodilators, stimulates the production and secretion of several hormones, including glucagon, insulin and growth hormone. In one or more embodiments, the vasodilator ingredient includes diarginine malate. The diarginine malate can be provided in an amount of 10 to 30 percent by weight, 12.5 to 25 percent by weight, or 15 to 20 percent by weight of the total weight of the admixture.

In one or more embodiments, the dietary composition further includes taurine, or 2-aminoethanesulfanic acid, which is an organic amino acid that is abundant in the tissues of many animals. Taurine compounds are also found in plants, fungi, and some bacterial species, but typically at lower levels. Taurine is a derivative of the sulfur-containing amino acid, cysteine. In some studies, there has been a link made between taking a suitable dose of taurine and weight loss in rats. Taurine can be provided in an amount of 1.0 to 4.0 percent by weight, 1.5 to 3.5 percent by weight, or 2.0 to 3.0 percent by weight of the total weight of the admixture.

In one or more embodiments, the dietary composition further includes *rhodiola*. *Rhodiola*, which is also known as "golden root" or "roseroot," is a plant in the family crassulaceae that grows in cold regions of the world such as Russia and Scandinavia. *Rhodiola* has certain effects in improving mood and alleviating depression. There are numerous animal and test tube studies that *rhodiola* has both a stimulating and a sedating effect on the central nervous system, depending on the intake amount. Moreover, *rhodiola* may enhance physical endurance; improves thyroid, thymus and adrenal function; protects the nervous system, heart and liver; and has antioxidant and anticancer properties. In certain particular embodiments, the Holarctic species of *rhodiola*, *Rhodiola rosea*, is used. In one or more embodiments, the *rhodiola* may include 3% active ingredient. *Rhodiola* can be provided in an amount of 0.05 to 20.0 percent by weight, 0.5 to 10.0 percent by weight, or 2.0 to 3.0 percent by weight of the total weight of the admixture.

In one or more embodiments, the dietary composition further includes extract of green tea. Green tea extracts can be herbal derivatives from green tea leaves, *Camellia sinensis*, containing antioxidants mainly in the form of catechins. The catechins include four major epicatechin derivatives including epicatechin, epigallocatechin, epicatechin gallate, and epigallocatechin gallate. Green tea is a "true" tea which has undergone minimal oxidation during processing. Its active substances of interest include polyphenols. The polyphenols are believed to be responsible for most of green tea's role in health. Research indicates that polyphenols may have antioxidant characteristics. When provided in dry solid form such as dry powder, dry pellets, or dry granules, the green tea extract can be provided in an amount of 1.0 to 4.0 percent by weight, 1.5 to 3.5 percent by weight, or 2.0 to 3.0 percent by weight of the total weight of the admixture.

In one or more embodiments, the term "extract" refers to a substance or composition obtained from one or more green tea plant parts, regardless of whether the substance or composition is found external to the green tea plant parts (i.e., an exudate). Chemical and/or physical action, as would be understood in the art, may be required to obtain the substance or composition from the green tea plant parts. While the green tea extract is preferably in the dry solid form as described herein above, the green tea extract can also be in liquid form, such as the so-called tincture. When the green tea extract is added to the admixture or the dietary composition thereof in the liquid form or as a tincture, according to one or more embodiments of the present invention, the amount of liquid or tincture added is equivalent to the dry extract solids amount as specified hereinabove. Alternatively, the liquid or tincture form of the green tea extract can be filtered, solidified, and/or dried using conventional methods such as filter concentration followed by vacuum drying.

In one or more embodiments, the dietary composition further includes dimethylethanolamine ("DMAE"). Dimethylethanolamine is related to choline and is a chemical precursor to the neurotransmitter acetylcholine. It is believed that dimethylaminoethanol is methylated to produce choline in the brain. This compound has also been referred to as N,N-dimethyl-2-aminoethanol, beta-dimethylaminoethyl alcohol, beta-hydroxyethyldimethylamine and Deanol. It is a liquid with a color that ranges from clear to pale yellow. Studies have shown an increase in vigilance and alertness, with a positive influence on mood, based on the use of dimethylethanolamine. In one or more embodiments, the DMAE is DMAE bitartrate. DMAE can be provided in an amount of 0.5 to 3.0 percent by weight, 1.0 to 2.5 percent by weight, 1.5 to 2.0 percent by weight of the total weight of the admixture.

In one or more embodiments, the dietary composition further includes inositol, or cyclohexane-1,2,3,4,5,6-hexol. The inositol suitable for use in the dietary compositional can include one or more of nine possible stereoisomers, namely myo-, scyllo-, muco-, chiro-, neo-, allo-, epi-, and cis-inositols. Inositol is a polyalcohol similar to a member of the B vitamin complex but it is not a B vitamin since it does not contain nitrogen. Some preliminary results of studies on inositol supplements show promising results for people suffering from problems such as bulimia, panic disorder and bipolar depression. The inositol can be provided in an amount of 0.05 to 2.0 percent by weight, 0.20 to 1.5 percent by weight, or 0.40 to 1.0 percent by weight of the total weight of the admixture.

In one or more embodiments, the dietary composition further includes vitamin C, or ascorbic acid, which is an organic acid with antioxidant properties. Animal studies suggest that supplementing with vitamin C can reduce blood levels of stress-related hormones and other measures of stress controlled studies of athletes have shown that vitamin C supplementation (1,000 to 1,500 mg per day) can reduce stress hormone levels after intense exercise. The vitamin C can be provided in an amount of 0.5 to 3 percent by weight, 0.75 to 2.5 percent by weight, 1.0 to 2.0 percent by weight, or 1.25 to 1.75 percent by weight of the total weight of the admixture.

In one or more embodiments, the dietary composition further includes one or more B vitamins. Non-limiting examples of B vitamins include vitamin B1 (thiamin or thiamin mononitrate), vitamin B2, vitamin B3 (niacinamide), vitamin B5 (pantothenic acid), vitamin B6 (pyridoxine), vitamin B7 (biotin), vitamin B9 and vitamin B12 (cyanocobalamin). The B vitamins often work together to deliver a number of health benefits to the body. Together, one or more B vitamins may work to combat the symptoms and causes of stress, depression and cardiovascular disease. In certain particular embodiments, the one or more B vitamins are provided in a B vitamin blend including the following components: vitamin B1, B3, B5, B6, B7, and B12. The B vitamin blend may contain vitamin B1 (15 mg), vitamin B2 (15 mg), vitamin B3 (50 mg), vitamin B6 (10 mg), vitamin B12 (10 mcg), pantothenic acid B6 (23 mg), folic acid B9 (400 mcg) vitamin C (500 mg), biotin (150 mcg), and minerals, calcium, magnesium and zinc, for combating stress effects. The vitamin B can be provided in an amount of 0.25 to 3 percent by weight, 0.5 to 2.5 percent by weight, 0.75 to 2.0 percent by weight, or 1.0 to 1.5 percent by weight of the total weight of the admixture.

In one or more embodiments, the dietary composition further includes a flowing agent such as Maltrin 510 and Maltrin QD 500 (a maltodextrin). The flowing agent helps to absorb moisture, and therefore eases the packaging process of the formulation ingredients. The resulting formulation has a relatively high level of dispersability in liquids, therefore minimizes clumping which may occur with formulations that do not include a flowing agent. Further, the flowing agent has been found to soften the flavor of the resulting diet drink supplement. The flowing agent such as Maltrin 510 can be provided in an amount of 3.0 to 6.5 percent by weight, 3.5 to 6.0 percent by weight, or 4.0 to 5.5 percent by weight, or 4.5 to 5.0 percent by weight of the total weight of the admixture.

In one or more embodiments, the dietary composition further includes one or more citrulline, a key intermediate in the urea cycle. In certain particular instances, the dietary composition further includes a di-citrulline malate which can be a mixture of citrulline. Without being limited to any theory, it is believed that citrulline malate may reduce the sensation of fatigue by increasing oxidative ATP synthesis and hence energy production. The di-citrulline malate can be provided in an amount of 1.5 to 30 percent by weight, 5.0 to 2.0 percent by weight, 7.5 to 12.5 percent by weight of the total weight of the admixture.

In one or more embodiments, the dietary composition further includes ATP (adenosine triphophate). When employed, the ATP can be provided in an amount of 0.01 to 4.0 percent by weight, 0.1 to 1.0 percent by weight, or 0.2 to 0.5 percent by weight of the total weight of the admixture.

In one or more embodiments, the dietary composition further includes Trehalose (Cargill) fine granular. When employed, the Trehalose (Cargill) fine granular can be provided in an amount of 25 to 75 percent by weight, 35 to 65 percent by weight, or 45 to 55 percent by weight of the total weight of the admixture.

In one or more embodiments, the dietary composition further includes sucrose (natural crane sugar). When employed, sucrose can be provided in an amount of 1.5 to 30 percent by weight, 5.0 to 20 percent by weight, or 10.0 to 15.0 percent by weight of the total weight of the admixture.

In one or more embodiments, the dietary composition further includes vitamin C (sodium ascorbate). When employed, vitamin C can be provided in an amount of 0.1 to 15 percent by weigh, 0.5 to 10 percent by weight, or 1.0 to 2.0 percent by weight of the total weight of the admixture.

In one or more embodiments, the dietary composition further includes natural passionfruit flavor #1231 sw. When employed, the natural passionfruit flavor #1231 sw can be provided in an amount of 2.5 to 17.5 percent by weight, 5.0 to 15.0 percent by weight, or 7.5 to 12.5 percent by weight of the total weight of the admixture.

In one or more embodiments, the dietary composition further includes malic acid, optionally in fine granules. When employed, malic acid can be provided in an amount of 1.0 to 12.0 percent by weight, 2.0 to 10.0 percent by weight, or 4.0 to 6.0 percent by weight of the total weight of the admixture.

In one or more embodiments, the dietary composition further includes glucuronolactone, optionally in fine granules. When employed, glucuronolactone can be provided in an amount of 0.1 to 15 percent by weigh, 0.5 to 10 percent by weight, or 1.0 to 2.0 percent by weight of the total weight of the admixture.

In one or more embodiments, the dietary composition further includes grape seed extract, for instance, grape seed extract by the name of *Vitis vinifera*. When employed, grape seed extract can be provided in an amount of 0.05 to 20.0 percent by weight, 0.1 to 10.0 percent by weight, or 0.6 to 1.0 percent by weight of the total weight of the admixture.

In one or more embodiments, the dietary composition further includes *Panax Ginseng*, for instance, *Ginseng* having 20% ginsenosides. When employed, *Panax Ginseng* can be provided in an amount of 0.05 to 6.5 percent by weight, 0.2 to 2.0 percent by weight, or 0.5 to 0.8 percent by weight of the total weight of the admixture.

In one or more embodiments, the dietary composition further includes Theanine from green tea. When employed, Theanine from green tea can be provided in an amount of 0.05 to 6.5 percent by weight, 0.2 to 2.0 percent by weight, or 0.5 to 0.8 percent by weight of the total weight of the admixture.

In one or more embodiments, the dietary composition further includes vitamin E, particularly vitamine E 50% CWS 50% RDI. When used, vitamin E is provided in an amount of 0.001 to 4.0 percent by weight, 0.01 to 2.0 percent by weight, or 0.2 to 0.6 percent by weight of the total weight of the admixture.

In one or more embodiments, the dietary composition further includes acesulfame K, optionally in fine crystals. When employed, acesulfame K can be provided in an amount of 0.1 to 1.2 percent by weight, 0.3 to 0.9 percent by weight, or 0.4 to 0.6 percent by weight of the total weight of the admixture.

In one or more embodiments, the dietary composition further includes one or more of the following additional ingredients: Rebaudioside A, Talin MD 90 as a natural sweetener, Resveratrol (Protykin™) 200:1 extract, black pepper extract (Bioperine™). When used, each one of these additional ingredients can be provided in an amount of 0.005 to 0.6 percent by weight, 0.01 to 0.4 percent by weigh, or 0.02 to 0.2 percent by weight of the total weight of the admixture.

EXAMPLE 1

A diet supplement for increasing energy and mental alertness in an individual, e.g., a human or an animal, during periods of fatigue or drowsiness, is provided. The diet drink supplement includes per 16 fluid ounce serving about 45 mg of Caffeine Anhydrous, about 750 mg Arginine (Diarginine malate), about 100 mg of Taurine, about 100 mg *Rhodiola* Extract, about 100 mg of an extract of Green Tea Leaf (50% Polyphenols), about 26 mg Inositol; and the following vitamins:

TABLE 1

| Vitamin | Amount Per Serving | RDI Value |
| --- | --- | --- |
| Vitamin C | 60 mg | 100% |
| Thiamin B1 | 3 mg | 200% |
| Riboflavin B2 | 1.7 mg | 100% |
| Niacin | 20 mg | 100% |
| Vitamin B6 | 6 mg | 300% |
| Vitamin B12 | 12 mcg | 200% |
| Biotin | 300 mcg | 100% |
| Pantothenic Acid | 20 mg | 200% |

In addition, the concentrate may contain sodium bicarbonate, sodium carbonate (for effervescence), natural flavor, other flavorings, aspartame with AcesulfameK or sucralose, (sweetener), and natural color.

As a diet supplement, at least eight (8) fluid ounces (or sixteen (16) fluid ounces in certain embodiments) of the beverage consumed orally during periods of fatigue or drowsiness or alternatively during periods wherein the user is in need of heightened mental alertness or physical energy. Each eight (8) fluid ounce serving may be consumed as needed throughout the day.

EXAMPLE 2

A diet supplement for increasing energy and mental alertness in an individual, e.g., a human or animal, is provided in powder packet form. Table 2 identifies the ingredients in each packet.

TABLE 2

| Ingredient | mg/packet | % w/w |
| --- | --- | --- |
| Citric Acid, anhydrous | 800 mg | 18.89 |
| Diarginine malate | 750 mg | 17.71 |
| Efferves-12F or Effersoda | 600 mg | 14.17 |
| Malic acid | 400 mg | 9.44 |
| Natural raspberry flavorant I | 200 mg | 4.72 |
| Natural raspberry flavorant II | 350 mg | 8.26 |
| Sodium citrate, fine granular | 200 mg | 4.72 |
| Maltrin 510 | 200 mg | 4.72 |
| Taurine | 100 mg | 2.36 |
| *Rhodiola* 3% | 100 mg | 2.36 |
| Green Tea 50% polyphenols | 100 mg | 2.36 |
| SweetAM | 100 mg | 2.36 |
| DMAE bitartrate | 75 mg | 1.77 |
| Vitamin C, 100% RDI | 65 mg | 1.53 |
| Dicaffeine malate | 60 mg | 1.42 |
| Sucralose | 30 mg | 0.71 |
| AcesulfameK | 30 mg | 0.71 |
| Inositol | 26 mg | 0.61 |
| Niacinamide B3, 100% RDI | 20 mg | 0.47 |
| Pantothenic acid, 200% RDI | 20 mg | 0.47 |
| Pyridoxine (HCl) B6, 300% RDI | 6 mg | 0.14 |
| Thiamin (mononitrate) B1, 200% RDI | 3 mg | 0.07 |
| Biotin, 100% RDI | 0.3 mg | 0.01 |
| Beet Juice Colorant | 0.1 mg | 0.00 |
| Vita B12 (cyanocobalamin 1%) 200% RDI | 0.0012 mg | 0.00 |
| TOTAL | 4235.40 mg | 100.00 |

Diarginine Malate is available from Creative Compounds, LLC of Scott City, Mo. Efferves-12F and Effersoda is available from SPI Pharma, Inc. of Wilmington, Del. Natural raspberry flavorant I is type 916730, available from Frutarom, Ltd. of Haifa, Israel. Natural raspberry flavorant II is #906.0089U/EN, available from FONA International of Geneva, Ill. Maltrin 510 is available from Grain Processing Corp. of Muscatine, Iowa. *Rhodiola* 3% is available from Draco Natural Products, Inc. of San Jose, Calif. Green Tea 50% polyphenols is available from Draco Natural Products, Inc. of San Jose, Calif. SweetAM is available from FONA International of Geneva, Ill. The DMAE bitartrate is available as D0090 product number from Novel Ingredients Services of Venice, Calif. The dicaffeine malate is available from Creative Compounds, LLC of Scott City, Mo. The beet juice colorant is available as 03600 product number from Sensient Technologies Corp. of Milwaukee, Wis.

A single packet is added to 16 ounces of water to produce a single serving of the diet drink supplement. The resulting mixture has mild fizz and sweetness and a relatively light color, and has a raspberry flavor. As a diet supplement, at least eight (8) fluid ounces (or sixteen (16) fluid ounces in certain embodiments) of the beverage can be consumed orally during periods of fatigue or drowsiness or alternatively during periods wherein the user is in need of heightened mental alertness or physical energy. Each eight (8) fluid ounce serving may be consumed as needed throughout the day.

EXAMPLE 3

A dietary supplement for increasing energy and mental alertness in an individual, e.g., a human or animal, is provided in powder packet form. Table 3 identifies the ingredients in each packet.

TABLE 3

| Ingredient | mg/packet | % w/w |
|---|---|---|
| Citric Acid, anhydrous | 800 mg | 18.89 |
| Diarginine malate | 750 mg | 17.71 |
| Efferves-12F or Effersoda | 600 mg | 14.17 |
| Malic acid | 400 mg | 9.44 |
| Natural lemon flavorant I | 350 mg | 8.26 |
| Natural lemon flavorant II | 200 mg | 4.72 |
| Sodium citrate, fine granular | 200 mg | 4.72 |
| Maltrin 510 | 200 mg | 4.72 |
| Taurine | 100 mg | 2.36 |
| *Rhodiola* 3% | 100 mg | 2.36 |
| Green Tea 50% polyphenols | 100 mg | 2.36 |
| SweetAM | 100 mg | 2.36 |
| DMAE bitartrate | 75 mg | 1.77 |
| Vitamin C, 100% RDI | 65 mg | 1.53 |
| Dicaffeine malate | 60 mg | 1.42 |
| Sucralose | 30 mg | 0.71 |
| AcesulfameK | 30 mg | 0.71 |
| Inositol | 26 mg | 0.61 |
| Niacinamide B3, 100% RDI | 20 mg | 0.47 |
| Pantothenic acid, 200% RDI | 20 mg | 0.47 |
| Pyridoxine (HCl) B6, 300% RDI | 6 mg | 0.14 |
| Thiamin (mononitrate) B1, 200% RDI | 3 mg | 0.07 |
| Biotin, 100% RDI | 0.3 mg | 0.01 |
| Beta-Carotene 1% | 0.01 mg | 0.00 |
| Vita B12 (cyanocobalamin 1%) 200% RDI | 0.0012 mg | 0.00 |
| TOTAL | 4235.31 mg | 100.00 |

Diarginine Malate is available from Creative Compounds, LLC of Scott City, Mo. Efferves-12F or Effersoda is available from SPI Pharma, Inc. of Wilmington, Del. Natural lemon flavorant I is #862.007, available from FONA International of Geneva, Ill. Natural lemon flavorant II is WONF, #2046104 available from Sensient Technologies Corp. of Milwaukee, Wis. Maltrin 510 is available from Grain Processing Corp. of Muscatine, Iowa. Rhodiola 3% is available from Draco Natural Products, Inc. of San Jose, Calif. Green Tea 50% polyphenols is available from Draco Natural Products, Inc. of San Jose, Calif. SweetAM is available from FONA International of Geneva, Ill. The DMAE bitartrate is available as D0090 product number from Novel Ingredients Services of Venice, Calif. The dicaffeine malate is available from Creative Compounds, LLC of Scott City, Mo. The beet juice colorant is available as 03600 product number from Sensient Technologies Corp. of Milwaukee, Wis.

A single packet is added to 16 ounces of water to produce a single serving of the diet drink supplement. The resulting mixture has mild fizz and sweetness and a relatively light color, and has a raspberry flavor. As a diet supplement, at least eight (8) fluid ounces (or sixteen (16) fluid ounces in certain embodiments) of the beverage consumed orally during periods of fatigue or drowsiness or alternatively during periods wherein the user is in need of heightened mental alertness or physical energy. Each eight (8) fluid ounce serving may be consumed as needed throughout the day.

EXAMPLE 4

A diet supplement for increasing energy, reducing soreness during and after workout routines, and/or increasing mental alertness in an individual, e.g., a human or animal, is provided in powder packet form. Table 4 identifies the ingredients in each packet.

TABLE 4

| Ingredient | mg/packet | % w/w |
|---|---|---|
| Trehalose (Cargill) fine granular | 4000 | 52.39 |
| Sucrose, fine granular | 1000 | 13.09 |
| di-citrulline malate, powdered | 750 | 9.82 |
| Natural Passionfruit flavor #123 sw | 700 | 9.17 |
| Malic acid, fine granular | 400 | 5.23 |
| Dicaffeine malate (100 mg caffeine) | 120 | 1.57 |
| Sodium ascorbate (100% Vitamin C) | 100 | 1.31 |
| Glucuronolactone, fine granular | 100 | 1.31 |
| *Rhodiola* Extract (3% Rosavins) | 75 | 0.98 |
| Grape seed extract (*Vitis vinifera*) | 60 | 0.78 |
| Sweet AM, natural flavor | 50 | 0.65 |
| Panax Ginseng (20% ginsenosides) | 50 | 0.65 |
| Theanine (from green tea) | 50 | 0.65 |
| Acesulfame K, fine crystals | 40 | 0.52 |
| Vitamin E 50% CWS, 50% RDI | 33 | 0.43 |
| ATP (adenosine triphosphate) | 25 | 0.33 |
| Niacinamide B3, 100% RDI | 21 | 0.28 |
| Rebaudioside A (Rebiana or Reb-A 97%) | 30 | 0.39 |
| Pantothenic acid, 100% RDI, calcium salt | 11 | 0.14 |
| Talin MD 90 (thaumatin) (natural sweetener) | 5 | 0.07 |
| Reveratrol (ProtykinTM) 200:1 extract | 4 | 0.05 |
| Black pepper extract (BioperneTM) | 4 | 0.05 |
| Riboflavin (R-5-phosphate) 200% RDI | 3.5 | 0.04 |
| Pyridoxine (HCL) B6, 100% RDI | 2.1 | 0.03 |
| Thamin (monoitrate) B1, 100% RDI | 1.6 | 0.02 |
| TOTAL | 7635.20 mg | 100.00 |

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed:

1. A dietary composition comprising:
    a therapeutically effective amount of an admixture including:
        a caffeine ingredient including dicaffeine malate of 0.1 to 15 percent by weight of the total weight of the admixture;
        a vasodilator ingredient; and
        *rhodiola rosea*.

2. The dietary composition of claim 1 further comprising an additive selected from the group consisting of taurine, green tea extract, dimethylethanolamine, inositol, vitamin C, one or more B vitamins, a flowing agent, citrulline malate, and combinations thereof.

3. The dietary composition of claim 1, wherein the dicaffeine malate is in an amount of 0.5 to 3.0 percent by weight of the total weight of the admixture.

4. The dietary composition of claim 1, wherein the vasodilator ingredient includes diarginine malate.

5. The dietary composition of claim 4, wherein the diarginine malate is in an amount of 10 to 30 percent by weight of the total weight of admixture.

6. The dietary composition of claim 1 formulated as a water-based dietary drink containing 3.0 to 5.0 grams of the admixture in dry power per 5 to 20 ounces of water.

7. The dietary composition of claim 2, wherein the additive includes taurine in an amount of 1.0 to 4.0 weight percent of the total weight of the admixture.

8. The dietary composition of claim 1, wherein the *rhodiola rosea* is of an amount of 0.05 to 20.0 weight percent of the total weight of the admixture.

9. The dietary composition of claim 2, wherein the additive includes green tea extract in an amount of 1.0 to 4.0 weight percent of the total weight of the admixture.

10. The dietary composition of claim 2, wherein the additive includes inositol in an amount of 0.05 to 2.0 weight percent of the total weight of the admixture.

11. The dietary composition of claim 2, wherein the additive includes dimethylethanolamine in an amount of 0.5 to 3.0 weight percent of the total weight of the admixture.

12. The dietary composition of claim 2, wherein the additive includes vitamin C in an amount of 0.5 to 3.0 weight percent of the total weight of the admixture.

13. The dietary composition of claim 2, wherein the additive includes B vitamins in a collective amount of 0.5 to 3.0 weight percent of the total weight of the admixture.

14. The dietary composition of claim 2, wherein the additive includes a flowing agent in an amount of 4 to 5.5 weight percent of the total weight of the admixture.

15. The dietary composition of claim 2, wherein the additive includes di-citrulline malate.

16. A dietary composition comprising:
a therapeutically effective amount of an admixture including:
dicaffeine malate of 0.1 to 15 percent by weight of the total weight of the admixture;
diarginine malate; and
taurine; and
*rhodiola rosea*.

17. The dietary composition of claim 16 further comprising an additive selected from the group consisting of green tea extract, dimethylethanolamine, inositol, vitamin C, one or more B vitamins, a flowing agent, and citrulline malate, and combinations thereof.

18. A method of alleviating a symptom of physical lethargy in a subject, comprising:
administering to the subject a therapeutically effective amount of a dietary admixture including: caffeine ingredient including dicaffeine malate of 0.1 to 15 percent by weight of the total weight of the admixture; a vasodilator ingredient; and *rhodiola rosea*.

19. The method of claim 18, wherein the dietary admixture is configured to further include an additive selected from the group consisting of taurine, *rhodiola*, a green tea extract, dimethylethanolamine, inositol, vitamin C, one or more B vitamins, a flowing agent, citrulline malate, and combinations thereof.

* * * * *